(12) United States Patent
Wise

(10) Patent No.: US 7,690,276 B1
(45) Date of Patent: Apr. 6, 2010

(54) HIGH-EFFICIENCY AIR INTAKE FOR AEROSOL AIR SAMPLERS

(75) Inventor: Daniel G. Wise, Ellicott City, MD (US)

(73) Assignee: The United States of America as represented by the Secretary of the Army, Washington, DC (US)

( * ) Notice: Subject to any disclaimer, the term of this patent is extended or adjusted under 35 U.S.C. 154(b) by 240 days.

(21) Appl. No.: 11/946,092

(22) Filed: Nov. 28, 2007

(51) Int. Cl.
*G01N 1/00* (2006.01)
(52) U.S. Cl. .................................. 73/864.33
(58) Field of Classification Search .......... 73/864.33, 73/864.73, 864, 864.34, 864.41
See application file for complete search history.

(56) References Cited

U.S. PATENT DOCUMENTS 5,040,424 A * 8/1991 Marple et al. ............ 73/863.23

* cited by examiner

*Primary Examiner*—Hezron Williams
*Assistant Examiner*—Nathaniel Kolb
(74) *Attorney, Agent, or Firm*—Ulysses John Biffoni

(57) ABSTRACT

The present invention relates to a method and apparatus for redirecting a flow of aerosol-containing air into, for example, an aerosol sampler. The apparatus comprising a device for redirecting a portion of the flow of aerosol-containing air into an air intake disposed within the flow of aerosol-containing air, preferably using eduction caused by a pressurized gas stream. A sampling tube having an opening for receiving aerosol-containing air is disposed within the air intake to collect the redirected portion of aerosol containing air.

6 Claims, 7 Drawing Sheets

Figure 1:
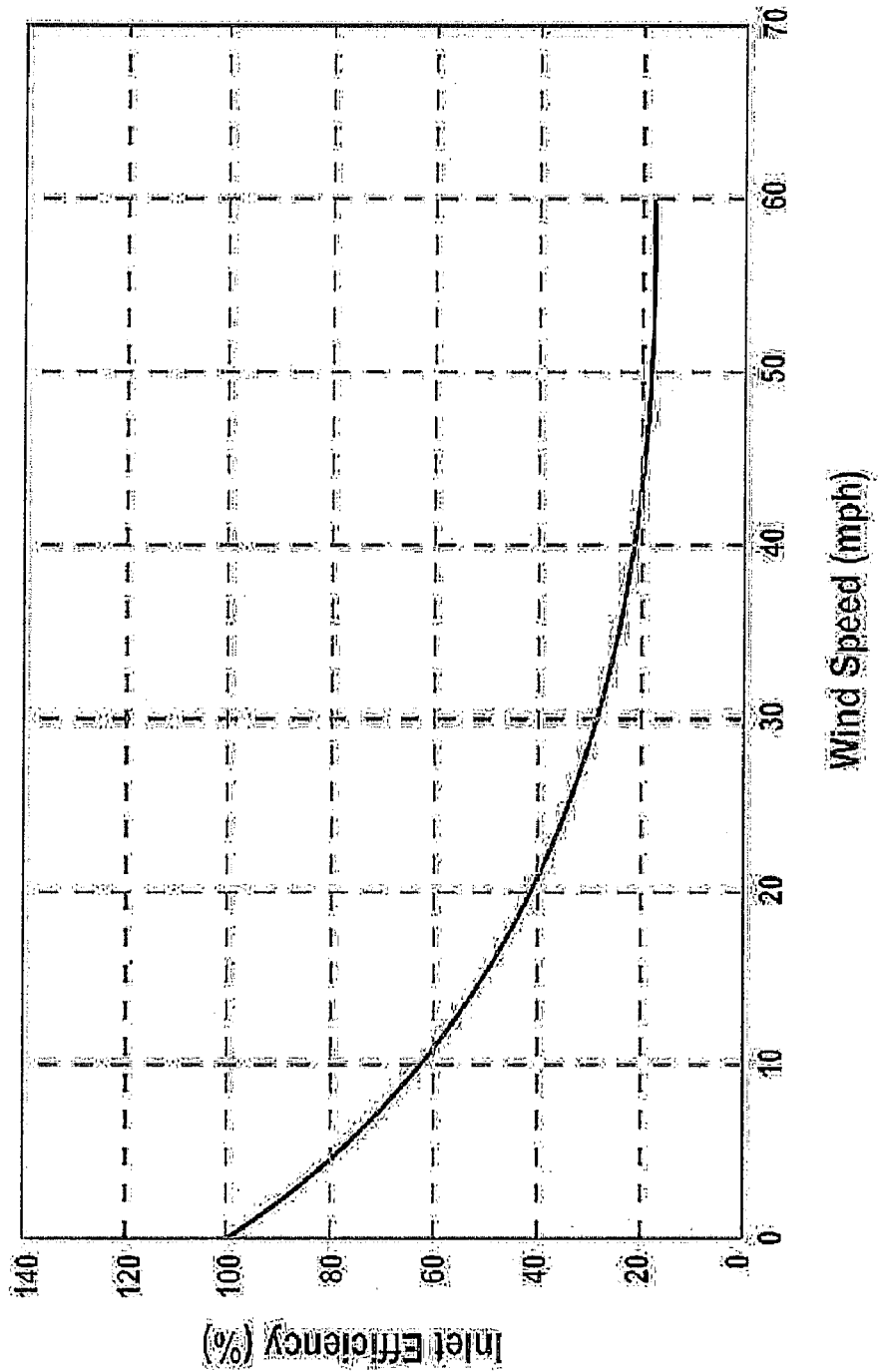

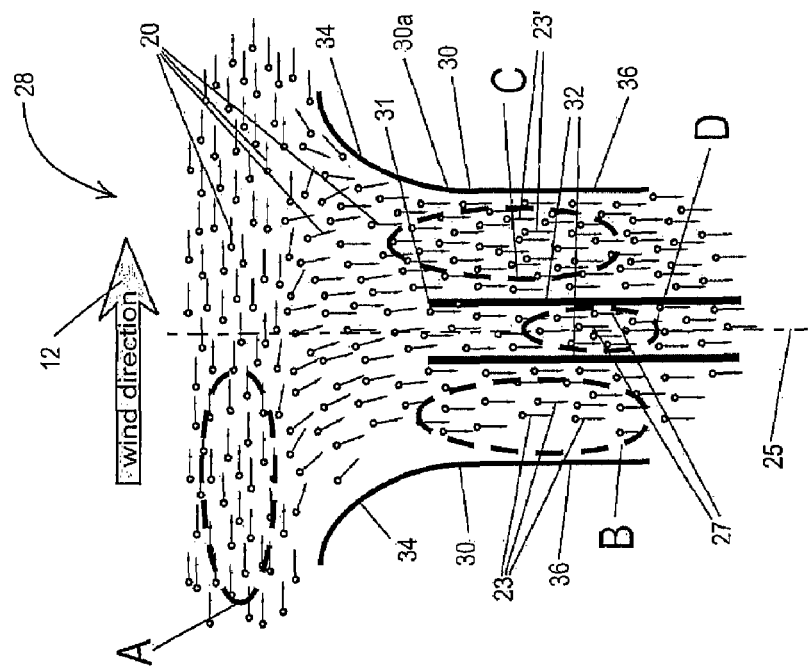
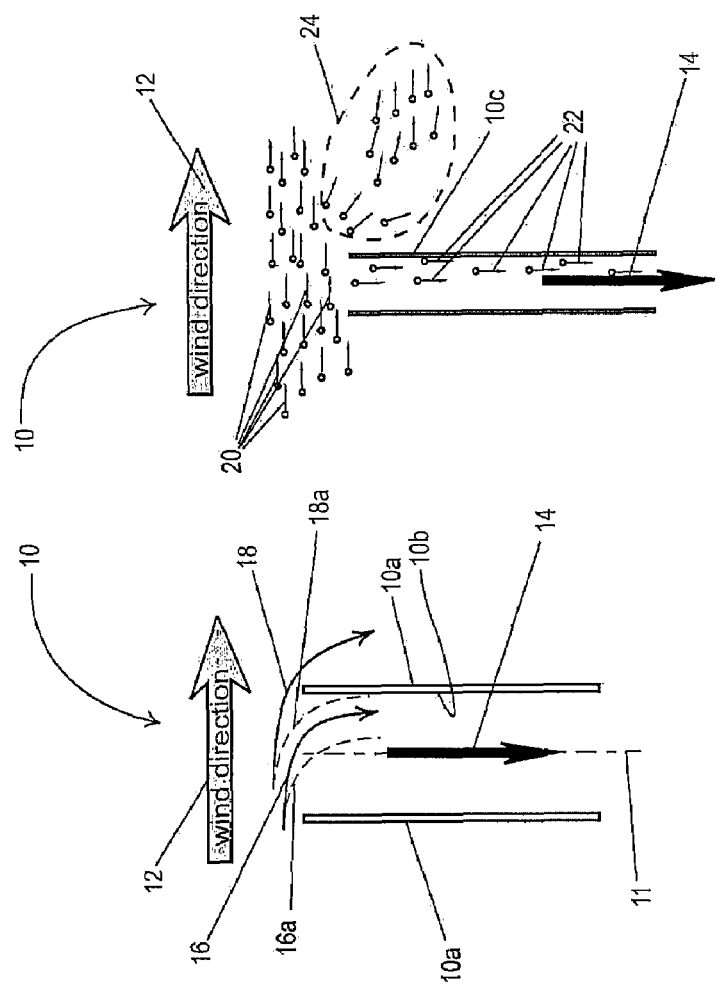
FIGURE 2A  FIGURE 2B  FIGURE 2C

HIGH-EFFICIENCY AIR INTAKE FOR AEROSOL AIR SAMPLERS

GOVERNMENT INTEREST

The invention described herein may be manufactured, used and licensed by or for the United States Government.

FIELD OF THE INVENTION

The present invention relates to air sampling and, in particular, sampling of air that contains aerosol particles. More specifically, the present invention relates to the taking of aerosol-containing air samples in settings where sharp changes of airflow direction in the vicinity of the intake of the air sampler can adversely affect the acquisition of airborne aerosol particles.

BACKGROUND OF THE INVENTION

Aerosols consist of small particles, liquid or solid, that are suspended in air. Airborne dust particles, virus particles and bacteria can also comprise an aerosol.

The study of aerosols has significance in many areas such as environmental and health studies, Homeland Security, and military defense, especially when the aerosol particles are pathogens. The device for collecting aerosol particles, commonly known as an aerosol sampler, is a critical component for these studies; its function is to collect aerosol-containing air and to characterize the concentration and type of the aerosol particles contained in the air.

Aerosol particles entrained in moving air have mass and velocity vectors—i.e., they have momentum—as they are collected for sampling. Because aerosol particles have inertia, they resist changes in their velocity vectors as their paths carry them into and through sampling collectors.

In a typical aerosol sampler, the aerosol-containing ambient air is first aspirated into the air sampler system through the air intake or inlet and thence transmitted to the rest of the sampler, sometimes through a system of transmission tubes or ducts, so as to convey the aerosol-containing air sample to the measurement portion of the aerosol-sampling device.

One of the basic performance parameters for an aerosol sampler is sampling efficiency. Overall sampling efficiency ($\eta_0$) is the ratio of amount of aerosol material in the collected sample ($C_{coll}$) to the amount of aerosol in the air ($C_{air}$) being sampled. It is usually calculated as the ratio of particles collected per volume of air sampled to the concentration (C) of particles in the ambient air.

$$\eta_0 = C_{coll}/C_{air}$$

The goal of unbiased aerosol air sampling is to measure the actual amount of aerosol, measured as the number of aerosol particles or as the weight of the airborne aerosol material, in an air sample that is as representative as possible of the air being sampled.

Aerosol air sampling often takes place in windy settings, wherein the sampled air has to be pulled from horizontal flow into a vertically oriented air intake. Because of the inertial aspects of aerosol particles, the change in direction from horizontal to vertical can cause a portion of the massive aerosol particles to overshoot the air intake and, also, to impact against, and lodge upon, the walls of the air intake sampling tube.

Therefore, a goal of aerosol air sampling is to collect air samples in such a way that $\eta_0$ is as close to 1 as possible, regardless of wind direction and speed or particle size. It may also be desirable for $\eta_0$ to be greater than 1 if one wants to maximize the amount of aerosol collected. A high-efficiency air intake is one that is resistant to the influence of wind upon collecting efficiency. A high efficiency air intake is important for the gathering of reliable aerosol air sampling data.

SUMMARY OF THE INVENTION

According to the present invention, there is disclosed an apparatus for redirecting a flow of aerosol-containing air, comprising an air intake disposed within the flow of aerosol-containing air, a structure for redirecting a portion of the flow of aerosol-containing air into the air intake, and a sampling tube having an opening for receiving aerosol-containing air disposed within the air intake.

Further according to the present invention, the structure for redirecting a portion of the flow of aerosol-containing air into the air intake comprises a source of pressurized gas, and a structure for injecting the pressurized gas into the air intake so as to cause the flow of the portion of aerosol-containing air in the air intake.

Also according to the present invention, the structure for injecting the pressurized gas into the air intake comprises an annular conduit within the air intake for directing the pressurized gas downstream of the opening of the sampling tube. The air intake comprises a converging inlet portion, an intermediate cylindrical portion and a diverging portion. The annular conduit is disposed within the intermediate cylindrical portion so that an inlet of the annular conduit receives the pressurized gas and an outlet of the annular conduit directs the pressurized gas past the opening of the sampling tube.

Still further according to the present invention, the source of pressurized gas is a manifold which receives the pressurized gas from the exhaust of an air sampling device.

Yet further according to the present invention, the air intake has a longitudinal axis extending therethrough and is circular thereabout.

Still further according to the present invention, the sampling tube has an inlet opening disposed within the cylindrical portion of the air intake. The sampling tube can have a shroud disposed about the inlet opening to direct aerosol-containing air into the sampling tube, and, generally speaking, the sampling tube, shrouded or unshrouded, is concentric with the longitudinal axis extending through the air intake.

Also according to the present invention, the structure for redirecting a portion of the flow of aerosol-containing air into the air intake comprises a gas pump disposed near an outlet opening of the diverging portion so as to cause the flow of the portion of aerosol-containing air in the air intake.

According to the present invention, there is disclosed a method for redirecting a flow of aerosol-containing air, comprising the steps of disposing an air intake within the flow of aerosol-containing air, redirecting a portion of the flow of aerosol-containing air into the air intake, and receiving aerosol-containing air within an inlet opening of a sampling tube.

Further according to the present invention, the step of redirecting a portion of the flow of aerosol-containing air into the air intake comprises the steps of providing a source of pressurized gas and injecting the pressurized gas into the air intake so as to cause the flow of the portion of aerosol-containing air in the air intake. The step of injecting the pressurized gas into the air intake comprises the step of directing the pressurized gas past the inlet opening of the sampling tube.

Still further according to the present invention, the method uses an air intake that comprises a converging inlet portion, an intermediate cylindrical portion and a diverging portion. An annular conduit is disposed within the intermediate cylindrical portion so that an inlet of the annular conduit receives the pressurized gas and an outlet of the annular conduit directs the pressurized gas past the opening of the sampling tube.

Yet further according to the present invention, the step of redirecting a portion of the flow of aerosol-containing air into the air intake comprises a step of disposing a gas pump disposed near an outlet opening of the diverging portion so as to cause the flow of the portion of aerosol-containing air in the air intake.

DEFINITIONS

"Aerosol" is defined herein as a dispersion of solid and liquid particles suspended in gas, including virus particles and bacteria.

"Eduction" is defined herein as the tendency of a flow of gas or liquid to entrain molecules that are adjacent to the flow. The mechanism of eduction derives from the inherent molecular motions of liquids and gases; that is to say, when a jet of, say, air is blown into a volume of stationary air, the motions of the molecules in the jet have a small forward velocity compared to the random thermal motions, which includes a lateral component that causes the jet molecules to engage stationary molecules and propel them in the direction of the jet flow. "Educted" flow refers to fluid motions imparted to ambient gases or liquids by a fluid jet.

"Air intake" refers to the basic invention described herein. It is an air intake for an aerosol sampling device. The terms "inlet," "air intake probe" and "intake probe" refer to the actual air inlet tube through which aerosol-laden air is drawn for analysis. The "inlet probe" is contained within the air intake and is generally concentric with it.

BRIEF DESCRIPTION OF THE DRAWINGS

The structure, operation, and advantages of the present invention will become apparent upon consideration of the description herein below taken in conjunction with the accompanying FIGURES. The FIGURES are intended to be illustrative, not limiting. Certain elements in some of the FIGURES may be omitted, or illustrated not-to-scale, for illustrative clarity.

Although the invention is generally described in the context of these preferred embodiments, it should be understood that the FIGURES are not intended to limit the spirit and scope of the invention to these particular embodiments.

The structure, operation, and advantages of the present preferred embodiment of the invention will become further apparent upon consideration of the following description taken in conjunction with the accompanying FIGURES, wherein:

FIG. 1 is a graph of intake efficiency of a typical vertically oriented sampling tube in horizontally moving wind;

FIG. 2A is a schematic cross-sectional side view of a vertically oriented air sampling intake, illustrating the overshoot of aerosol particles when sampling in a wind;

FIG. 2B is a detailed schematic cross-sectional side view of a vertically oriented air sampling intake, illustrating aerosol particles and vectors when sampling in a wind;

FIG. 2C is a detailed schematic cross-sectional side view of a vertically oriented air sampling intake illustrating the sampling benefit of a flow-aligning duct;

FIG. 3A is a cross-sectional schematic side view of one embodiment of the present invention;

FIG. 3B is a cross-sectional schematic side view of the embodiment of the present invention shown in FIG. 3A, but with a shrouded inlet probe;

FIG. 4 is a cross sectional schematic illustration of the eduction gas-flow process shown in Section E of FIG. 3A; and FIG. 5 is a graph of the operating efficiency of the invention as a function of wind speed.

FIG. 6 is a schematic cross sectional view of another embodiment of the present invention.

DETAILED DESCRIPTION OF THE PREFERRED EMBODIMENTS

FIG. 1 is a curve of sampling efficiency, $\eta_0$, for a typical commercially available sampling inlet of an aerosol sampler, as a function of wind speed. Inlet efficiency is a primary concern in sampler design because it degrades significantly with increasing ambient wind. A significant increase in inlet performance is a cost-effective way to generate a proportional increase in point-detection system performance.

The dynamical aspect of degraded inlet efficiency in windy conditions is illustrated in FIGS. 2A and 2B. FIG. 2A is a schematic orthogonal cross-sectional view of a cylindrical tube air inlet 10 of an aerosol air sampling system (not shown). Wind direction is as indicated by the large arrow 12. The direction of air movement in the inlet tube 10*a* is as indicated by the large black arrow 14. Curved arrow 16 denotes the trajectory of an aerosol particle being diverted into the sampling tube 10, and dashed line 16*a* denotes the trajectory of the same aerosol particle if it had a mass equivalent to that of an oxygen or nitrogen molecule. That is to say, the aerosol particle's actual trajectory 16 has a larger radius of curvature than shown by the dashed line 16*a*, because of the aerosol's inertia, causing it, therefore, to move away from the motion of the air molecules.

Referring still to FIG. 2A, the actual and ideal trajectories 18 and 18*a*, respectively, of another particle are also shown, this time overshooting the wall 10*a* of the sampling tube 10. In other words, the actual trajectory 18 of an aerosol particle carries the particle beyond the wall 10*a*, whereas the dashed line 18*a* shows how the same particle would have entered the sampling tube if the aerosol particle following trajectory 18 were to have had no greater inertia than that of an oxygen molecule.

The tendency, as indicated in FIG. 2A, for the captured aerosol particles (e.g., as represented by the arrow 16), to have a velocity component that is normal to the axis 11 of inlet tube 10 also can cause a portion of the captured particles to impact against the inner wall surface 10*b* and adhere to it, thereby further degrading the collection efficiency of the inlet tube 10.

FIG. 2B is an orthogonal schematic representation of an inlet tube portion 10 showing the free-air movement of aerosol particles 20, along with directional components of their velocity vectors, in a wind denoted by the arrow 12. Note that the aerosol particles 22 that have been drawn into the sampling tube 10 are bunched on the down-wind side 10*c* of the tube, and that the concentration of the particles 22 within the tube is less than the free-stream concentration suggested by the concentration of aerosol particles indicated by the arrows 20. Those skilled in the art of fluid dynamics would be aware that at least some of the particles within the region encircles by the dashed line 24, located downstream of the sampling tube 10, would have been able to enter the tube 10 if their inertias had been close to that of the molecules of the sampled air.

FIG. 2C is an orthogonal schematic cross sectional representation of the basic principle of the present invention 28 disposed within an airflow containing aerosol particles 20. An enlarged circular air intake 30 is substantially concentric with a cylindrical sampling tube 32 which is essentially the same as the sampling tube inlet 10 in FIGS. 2A and 2B. Note that the circular air intake 30 has a converging duct portion 34 and a cylindrical portion 36, both of which are circular in aspect about and axis 25 which is perpendicular to the view of FIG. 2C. The horizontal paths of laterally moving aerosol particles 20 are reoriented, or redirected, toward vertical motion of the sort represented by arrows 23. In other words, the invention 28 causes a large sample of aerosol-laden horizontally moving air 20 to be reoriented into vertical motion when the air 20 is pulled into the large circular air intake 30. A portion of the reoriented air, represented by the arrow 27, is captured in the concentrically disposed sampling tube 32. The smoothly converging inlet portion 34 of the invention 28 works to reduce inlet turbulence.

Aerosol particles 20 are shown with arrows indicating the directional portions of their velocity vectors. The aerosol particles 20 that are shown moving with the wind 12 have a concentration that is graphically indicated by the particles contained within the region surrounded by dashed line A. The particles 20 that are inside the enlarged circular air intake 30 are bunched toward the down-wind side 30a of the enlarged circular air intake portion 30 of the present invention 28. Note, for instance, the aerosol particles 23 contained within the region indicated by dashed line B; their concentration is portrayed as less than that of the particles 20 contained within the region encircled by the dashed line A. The concentration of aerosol particles 23' in the region bounded by the dashed line C is, or plausibly would be to those skilled in the art, slightly greater than within the free-stream zone bounded by the dashed line A. The aerosol particles 27 that have been drawn into the central sampling inlet tube 32, and contained within the region bounded by the dashed line D, have an air concentration that is portrayed in FIG. 2C as equal to, or close to equal to, the concentration of the particles 20 contained within the free-stream bounded region indicated by the dashed line A. Furthermore, in normal ambient outdoor wind velocities, the aerosol concentration in region A should be approximately equal to the total concentration in regions B, C, and D combined.

In net effect, the present invention, as schematically demonstrated in the FIG. 2C, redirects the inlet flow of air from horizontal to vertical and aligns the flow of aerosol-burdened air 20 and 27 in such as way as to allow aerosol particles 27 to be captured in an air sampling inlet 32 in such as way as to minimally disturb, or otherwise influence, the free-stream aerosol-particle concentration as indicated within the region that is bounded by the dashed line A.

The invention thus far described also includes a means for redirecting a portion of the flow of aerosol-containing air into the air intake. More specifically, the basic concept of the present invention 28, as shown in FIG. 2C, shows a large volume of air being drawn into a large intake 30 that is concentric with the sampling tube 32. The invention envisions the means for redirecting the large volume of vertically moving air to preferably be the method of eduction, whereby a small flow of high-velocity gas induces the flow of a larger volume of gas. However, it is within the terms of the present invention to use other means and methods to induce the flow of a large volume of gas.

The mechanism of eduction can be envisioned by thinking of how a fluid jet into stationary air causes the jet to slow down as it conveys its momentum to the stationary air, which is correspondingly accelerated in the direction of said jet. The present invention 28 provides means for injecting pressurized gas into the air intake 30 so as to cause the flow of the portion of aerosol-containing air in the air intake.

The present invention is preferably related to eduction-induced flow because, as will become evident hereinbelow to those skilled in the art, the present invention is, intended to be retrofitted to the intake portions of existing sampling machines. It is also within the terms of the present invention to induce the larger flow within the larger tube 30, as illustrated by the particles and motion arrows 20 in FIG. 2C, by use of a fan or gas pump disposed far down stream of the inlet region 31 of the sample tube 30. While this arrangement might not be as easy to adapt to, or retrofit to, existing air sampling machines, nonetheless, it is within the terms of the invention that a gas pump or fan could be disposed near an outlet opening of the diverging portion 54 so as to cause the flow of the portion of aerosol-containing air in the air intake. It is thought that the educted-motion method of pumping air provides an elegant overall design that more easily allows retrofitting of the present invention to existing air-sampling hardware.

Figure 3A:
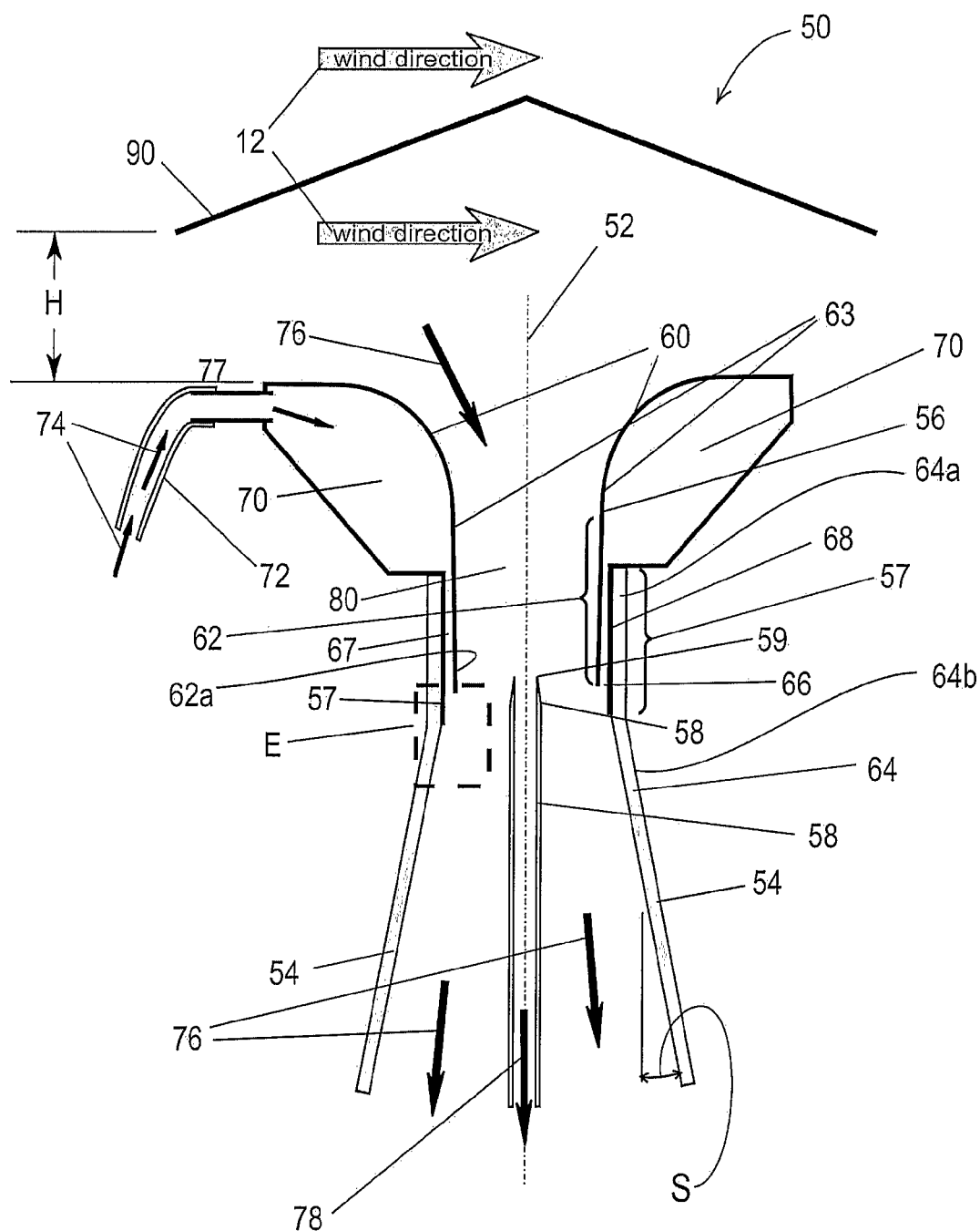

FIG. 3A is a schematic cross sectional view of an air intake system 50 according to the present invention. The air intake system 50, as shown in FIG. 3A, includes an air intake 63 that is circular in shape about a vertically oriented central longitudinal axis 52 extending there through. The air intake 63 includes three primary parts: a converging portion 60, a cylindrical portion 62, and a diverging portion 54, which also serves as an outlet for the redirected airflow.

The converging portion 60 of, air intake 63 has a curved shaped surface formed according to a curve rotation. The curve being of the set of curves that includes circles and parabolas. The gently curving inlet portion 60 converges with the cylindrical portion 62 to form a smooth surface so as to minimize the onset of turbulent flow within and downstream of the central flow region 80. The diverging portion 64 has a first section 64a that can extend parallel to the centerline 52 and a second diverging portion 64b that can begin diverging below the end 62a of the cylindrical portion 62 a distance of about six inches. The diverging portion 64b of the air intake 63 diverges from the axis 52 with an angle S of preferably about 3.5 degrees. It is, however, within the scope of the present invention that the angle of divergence can be 0 degrees, i.e., the cylindrical portion 62 of the air intake 63 can continue to extend downward and effectively form an extension of the circular cylinder portion 62.

An air inlet sampling tube 58 is disposed, preferably concentrically within diverging portion 54 and has an intake opening 59 disposed at the same level or about 10 centimeters above the bottom end 62a of the cylindrical portion 62 of the air intake 63. The opposite end of the air inlet sampling tube 58 is connected to an aerosol sampler, not shown.

A circular manifold 70, that can be concentric with the axis 52, has an annular nozzle 66 including a conduit 67, located inward from the first section 64a of diverging portion 64. The circular manifold 70 can be connected to a supply of eduction-driving air 74 by way of the tube 72. The tube 72 can communicate with a source of pressurized air, as described herein below.

Figure 4:
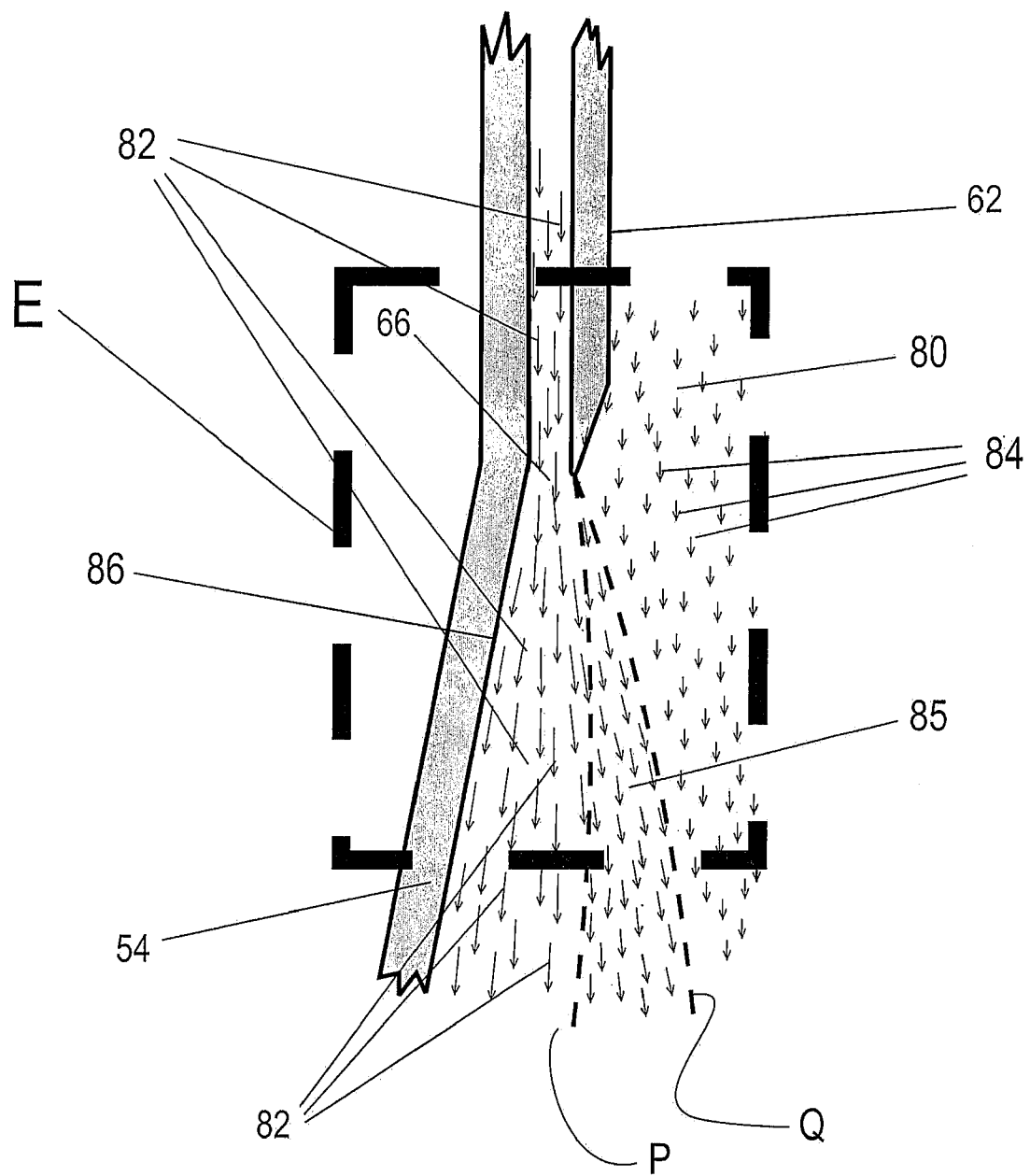

Referring to FIG. 4, there is shown an expanded view of the mixing region 85 about annular nozzle 66 (the mixing region is shown bounded by the dashed rectangle E in FIG. 3A). Mixing region 85, which is substantially annular in shape, is where the eduction effect is shown to take place downstream of the annular nozzle 66. The motive air indicated by the air velocity arrows 82, emerges from the annular nozzle 66 and entrains the downward-diverted aerosol containing air, indicated by the air velocity arrows 84, flowing within the central flow region 80. The motive air, indicated by the air velocity arrows 82, emerges from the annular nozzle 66. This annular flow provides a moving boundary layer between it and the aerosol laden air 84 and a low pressure zone which entrains the downward-diverted aerosol containing air. Therefore, a high volume flow of aerosol laden air is induced within region 80 in a substantially uniform way.

Note, that annular ring nozzle 66 (FIG. 3A) can create a thin moving air layer with very little pressure drop if desired. Accordingly, the velocity of the educted aerosol is controlled by the motive air flow rate and can be designed to present the aerosol to the sampling probe at air optimized velocity for either unbiased sampling (if the aerosol flow velocity matches the sampling probe intake velocity—known as isokinetic sampling), or to maximize aerosol collection by ramming the particles into the probe intake (a condition known as super-isokinetic sampling).

The source of pressurized air to drive the eduction effect in many commercial applications is generally a portable air compressor. However, in biological or environmental sampling applications as contemplated with respect to the present invention, this educting air flow may be readily supplied on a sampler's mounting platform, e.g., engine exhaust from a HUMVEE® (although contamination of the sampled air may be a concern in this scenario), or steam on a Navy ship.

It is also within the terms of the present invention to use an alternative source of pressurized air: i.e., reuse the energy already existing in the exhaust flow of the aerosol air sampler upon which the present invention is to be used. That is to say, most aerosol air samplers use a blower to draw air through the inlet and sampling system, and the exhausted air still has sufficient kinetic energy for use as to drive the eduction effect.

Such use of the exhausted gas from the air sampler does not affect the flow rate through the sampler. It is therefore within the terms of the present invention for the exhaust of the sampler (not shown), or a portion of the exhaust, to be re-routed to the annular collar manifold 70, by means of tube 72 which communicates between the manifold and the exhaust of the air sampler. This should be feasible if the pressure drop in the annular collar/manifold 70 is low so that it does not load the blower and reduce the primary flow 78 (FIG. 3A) which passes through the sampling system.

While the eduction method of pumping air can be achieved in an efficient way by injecting a curtain of gas from the annular opening of nozzle 66, it is within the terms of the invention that the eduction can also be achieved by the injection of pressurized gas from a one or more single circular nozzles into the flow of diverted aerosol-containing gas 76. In other words, the injection of a single jet of gas into the air intake 63 can transfer momentum to, and entrain, another gas, such as air, and, by the eduction process, cause air to move in the duct.

The overall result of eduction is a large increase in the volume flow rate of the inlet air by means of the use of a small volume of fast-moving air—in effect, a flow amplifier. The advantage of using the eduction effect in the present invention is that it initiates and maintains the flow indicated by the arrows 76 in FIGS. 3A, 3B and 84 in FIG. 4 without requiring the use of a large blower on the actual inlet region bounded by the flow surfaces 60. This method of inducing a gentle redirection of the horizontal wind-driven airflow into a vertical flow minimizes inertial losses of particles such that the concentration of air-entrained aerosol particles is minimally affected by the changed direction of the air that is sampled. The eduction force which draws the air can easily overpower the ambient wind force and therefore eliminate or severely mitigate the wind sensitivity of aerosol air samplers.

To summarize the basic concept: this aerosol sampling air intake device 50 uses eduction to redirect ambient air containing aerosol particles towards a directional sampling probe which is oriented in the direction of air flow through an air intake device 50. The eduction zone (see FIG. 4) is vertically oriented so that it aspirates, in an omni-directional fashion, large volumes of the ambient air.

A circular conical rain cover 90 is shown in FIG. 3A disposed over the top of the air-inlet portion 58, at an elevation H of between about 10 to about 20 centimeters, sufficient to not interfere with the movement of air there beneath. The rain cover 90 can be detachable from the main body of the air intake system 50. The conical shape of the rain cover 90 is merely illustrative, as other shapes clearly would suffice to block rain from falling onto the air intake system 50.

In the operation of air intake system 50, aerosol containing air to be sampled, as indicated by the arrows 76 of FIG. 3A, is drawn into the air intake 63 by means such as the method of the aforementioned eduction. That is, the manifold 70 directs pressurized gas into annular conduit 67. Being that the conduit 67 is located within the intermediate cylindrical portion 62, the pressurized gas is directed from the same height or below the inlet opening 59 and in the direction past of the sampling tube 58 to create a curtain of fast-moving air that is discharged through the annular nozzle 66 as an annular sheet of air moving in a downward direction, as illustrated in more detail in FIG. 3A. The aerosol-containing air 76 is drawn into the air intake 63 by the curtain of fast-moving pressurized gas. This causes the aerosol containing air to be sampled to be redirected into the air intake 63. Then the air that is captured in the air intake 63 moves downward towards the air sampling probe 58 and is captured in the probe for later evaluation, as indicated by the arrow 78. The sampling tube 58 has an inlet or opening 59 at the tube's upper most location through which sampled gases (indicated, roughly, by the arrows 76) are captured for delivery 78 into the air sampling machine (not shown).

It can now be appreciated that the air intake apparatus 50 of the present invention enables the redirecting of horizontal airflow into a downward-directed flow in such a way as to make a gentle turn from the horizontal plane where the wind is a variable to a vertical direction where the downward-directed flow has a constant direction and relatively constant velocity parallel to the vertically oriented axis 52 of the air intake 50.

The air intake system 50, thus far described, combines the enhanced inlet efficiency of a directional sampling probe inlet with the wind direction insensitivity of the prior art omni-directional inlet that comprises part of the method of achieving improved sampling efficiency. This will allow high efficiency, aerosol sampling from moving air from any direction without the need to articulate an inlet tube of an air intake device such that its axis is in approximate alignment with the prevailing wind-velocity vector. Since the wind vector variables exist mostly in a generally horizontal plane, omni-directional inlets are oriented vertically to maximize sampling efficiency and uniformity in conditions of wind from any direction. By orienting the inlet vertically however the flow must be turned 90 degrees downward, as should be apparent to those who are skilled in the art.

Prior to the air intake system 50 according to the present invention, many sampling inefficiencies would be incurred because of the inability of the prior art to redirect the flow necessary for omni-directional sampling, as indicated with the FIGS. 2A and 2B.

Figure 3B:
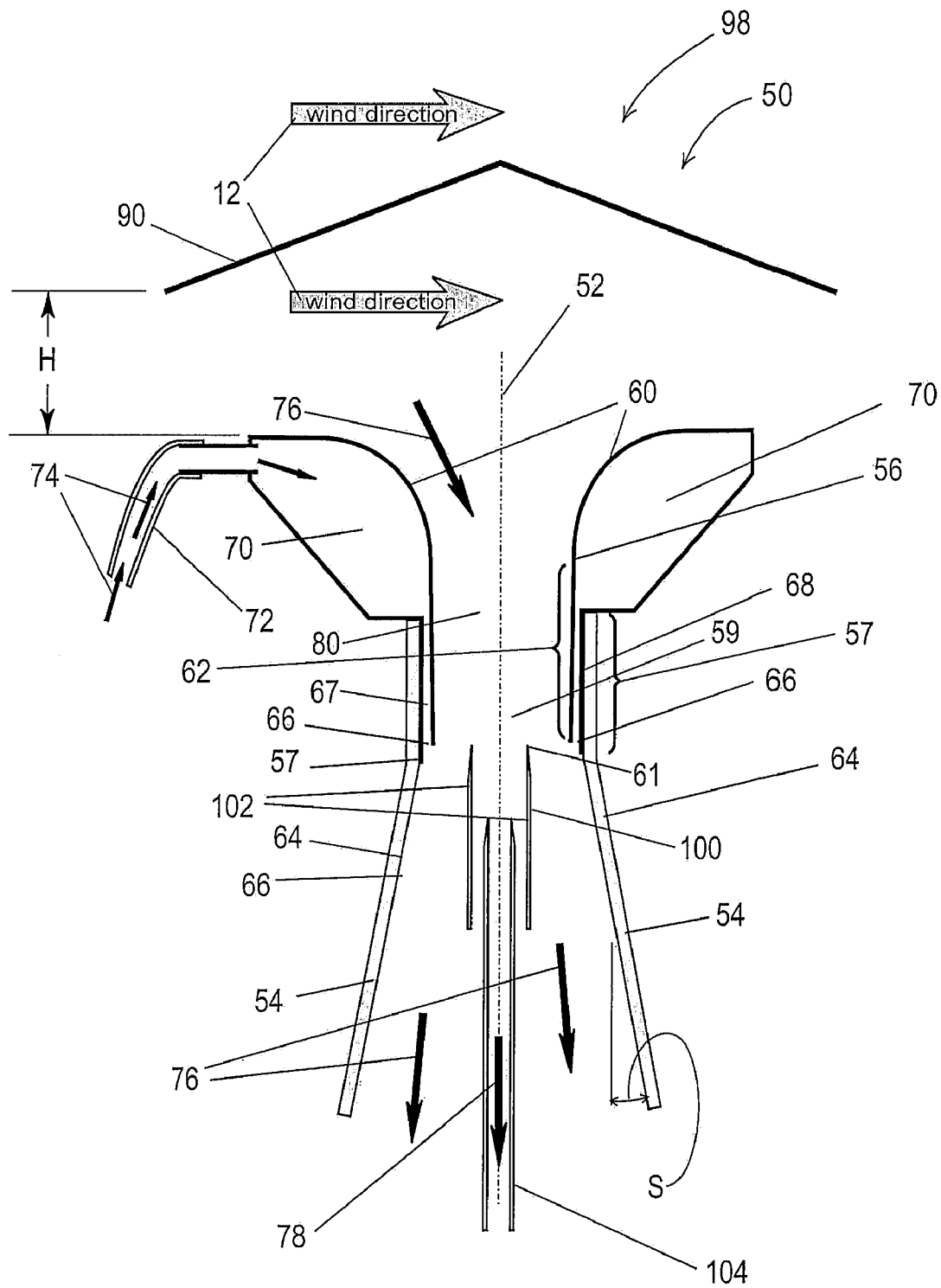

In an additional embodiment, an air intake apparatus 98, incorporates a shrouded probe 100, as illustrated in schematic fashion in FIG. 3B. The additional shrouded probe 100 can be used with the air intake apparatus 50 shown in FIG. 3A so as to insure, yet further, a high efficiency of collection of aerosol particles for sampling purposes. The shrouded probe 100 includes a shroud portion 102, which can be a circular cylindrical tube that surrounds and is concentric with an inlet tube 104 (compare inlet probe or tube 58 in FIG. 3A), having an intake opening 61. The shroud 102 provides the benefit of further aligning, in a vertical way and parallel to the axis 52, the movement of air to be sampled prior to its entering the inlet tube 104. It can be appreciated that the air intake apparatus 98 is substantially similar to the air intake system 50 shown in FIG. 3A, except for the addition of the shrouded probe 100 in FIG. 3B.

Testing

Two versions of the present invention were fabricated and tested in the U.S. Army's Edgewood Chemical Biological Center's Open-Jet Aerosol Wind Tunnel in 2006. The two versions differed only in terms of the source of pressuring air to drive the eduction effect.

One version used a commercial air eductor which is intended to ventilate flammable gasses from confined spaces and was powered by compressed air from an air compressor to power the eduction effect. Also, a shrouded inlet probe 104 (FIG. 3B) was used. The other version used exhaust air from the air sampling device (not shown in the FIGURES) to drive the eduction effect.

The initial test with the commercial eductor provided data that indicated that position of the probe relative to the annular collar of jets is important, probably because of turbulence from the jets (in the commercial eductor ventilator) in the bottom part of the eductors diffusing cone 54. Best results were obtained when the top of the shrouded probe was at or above the annular ring nozzle 66 that introduces the eductor flow. That is., referring to FIGS. 3A and 3B, the top-most portions 59 and 61 of the inlet tubes 58 and 100, respectively, should be disposed with respect to the annular eduction-air outlet 66 so that the top edges 59, 61 are located upstream of the annular outlet 66 a distance of about 10 to about 20 centimeters, or at least at the same elevation.

A second tested version was fabricated to examine the use of sampler exhaust air as the eduction flow driver. This requires a very low pressure drop through the annular eductor ring manifold 70, which, for this test, was custom fabricated from cardboard tubing. The biggest design difference between this eductor and the commercial air mover was that the commercial eductor uses an annular ring of jets which create a lot of back pressure, whereas this second prototype made of cardboard created this annular ring of air by using two concentric tubes with mostly open space between them (see 66 in FIG. 3A), resulting in no detectable pressure drop.

The wind tunnel tests were conducted at wind speeds of 5-15 mph (which are likely sampling environments for outdoor samplers) and the test particles had a monodisperse size distribution around 5-um aerodynamic diameter (which is a likely particle size of interest for bio-defense and environmental/heath sampling). The first version test used a sampling flow rate of 100 liters per minute (lpm), which is typical of current bio detection systems, and the second version test used a flow rate of 400 lpm which is also representative of current commercial samplers.

Figure 5:
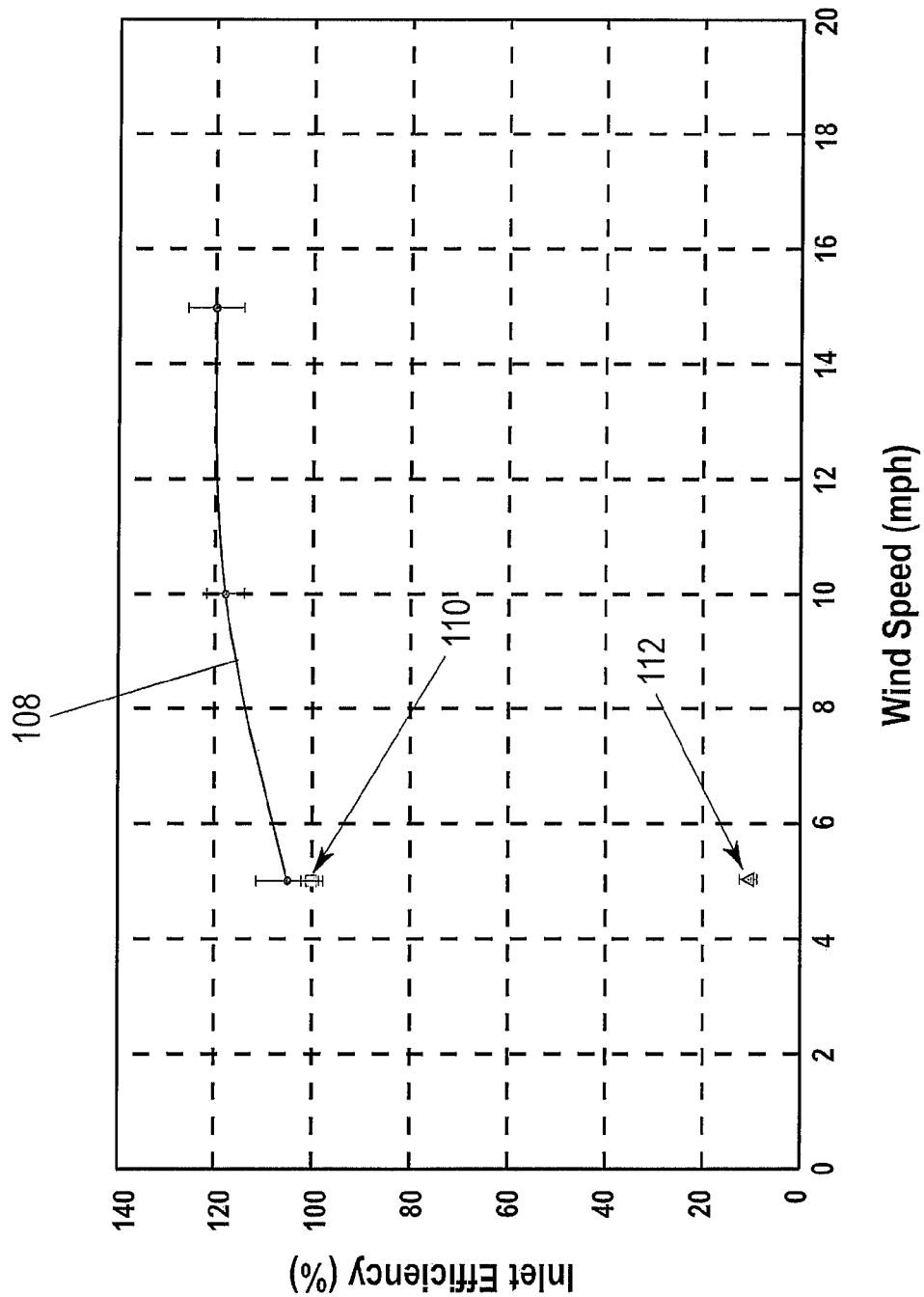

FIG. 5 is a graph summarizing the test results showing inlet efficiency as a function of wind speed. The line 108 shows the first test version wherein the eductor flow was supplied by a commercial eductor using 50 psi compressed air. Data point 110 came from a second test version wherein the eductor air flow was supplied by the air sampler exhaust. Data point 112 is from a second version test in which no eduction flow was used to drive the redirecting of flow of the air to be sampled.

The curve 108 shows air intake efficiency varying from 100 percent to 120 percent. This first version test used a commercial eduction air mover driven by compressed air. That the collection efficiency achieved efficiencies greater than 100 percent indicates an enrichment of the airstream took place as the large volume of educted flow is rammed with significant velocity into the shrouded sampling probe. Notice that the performance remains high over the tested wind velocity range, which is in contrast to the performance of a typical omnidirectional inlet shown in FIG. 1. The second test version, which uses recycled sampler exhaust air, was only tested at a 5-mph wind velocity. Notice that it also has a very high sampling efficiency, especially when compared to the operation of this inlet when the recycled eductor flow is not used. This direct comparison shows that the use of educted air flow into a sampling probe significantly increases inlet efficiency. These tests support the claims for this invention, that, first, the air-eduction collar manifold 70 coupled with a sampling probe 100 significantly increases inlet efficiency, and, second, this concept successfully mitigates or even eliminates inlet wind sensitivity over normal sampling wind speeds. Flow visualization dramatically demonstrated the premise that the educted air flow can easily overpower the wind vector and gently redirect fast moving air to the vertical orientation.

Figure 6:
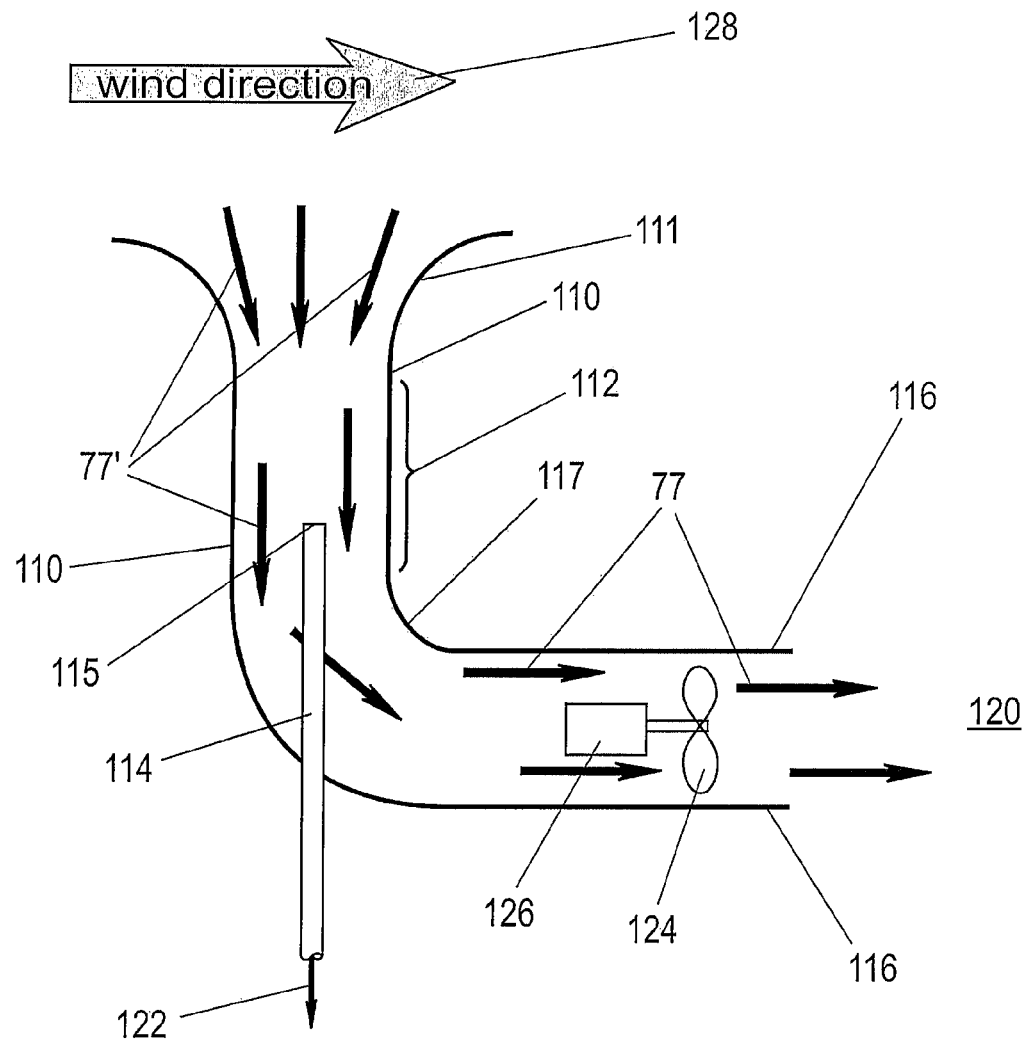

FIG. 6 is a schematic cross sectional view of another embodiment of the present invention comprising an air intake portion 110 having a converging portion 111 and a circular cylindrical portion 112, the air intake portion 110 being essentially the same as the air intake 30 shown in FIG. 2C. A vertically oriented sampling tube 114 is disposed coaxially with the cylindrical portion 112 in such a way that the opening 115 to the sampling tube is located about one-quarter of the way into the lower part of the cylindrical portion 112. The air intake 110 of this second embodiment includes bend 117 of about 90 degrees, such that said bend 117 communicates with a more or less horizontally disposed tail portion 116 through which air, indicated by arrows 77 exhausts to the outside 120. Air moves within the sampling tube 114 in the direction indicated by the arrow 122. Contained within the tail portion is a fan or like pump 124 driven by a motor 126 housed therein.

In net effect, the motor 126 and fan 124 exhaust air 77 and, in so doing, diverts, in a uniform way, a portion 77' of the windy aerosol-containing air 128 into the air intake embodiment 110, such that an aerosol-laden quantity of air 122 is able to be drawn into the intake tube 114.

Although the invention has been shown and described with respect to a certain preferred embodiment or embodiments, certain equivalent alterations and modifications will occur to others skilled in the art upon the reading and understanding of this specification and the annexed drawings. In particular, regard to the various functions performed by the above described air intake device for aerosol sampling systems, the terms (including a reference to a "means") used to describe such device are intended to correspond, unless otherwise indicated, to any device which performs the specified function of the described device (i.e., that is functionally equivalent), even though not structurally equivalent to the disclosed structure which performs the function in the herein illustrated exemplary embodiments of the invention. In addition, while a particular feature of the invention may have been disclosed with respect to only one of several embodiments, such feature may be combined with one or more features of the other embodiments as may be desired and advantageous for any given or particular application.

What is claimed is:

1. An apparatus for redirecting a flow of aerosol-containing air, comprising:
   an air intake disposed within the flow of aerosol-containing air;
   means for redirecting a portion of the flow of aerosol-containing air into the air intake; and
   a sampling tube having an opening for receiving aerosol-containing air disposed within the air intake;
   wherein the means for redirecting a portion of the flow of aerosol-containing air into the air take comprises: a source of pressurized gas; and means for injecting the pressurized gas into the air intake so as to cause a flow of the portion of aerosol-containing air in the air intake;
   wherein the means for injecting the pressurized gas into the air intake comprises: an annular conduit within the air intake for directing the pressurized gas downstream of the opening of the sampling tube;
   wherein air intake comprises: a converging inlet portion, an intermediate cylindrical portion and a diverging portion; and the annular conduit is disposed outside the intermediate cylindrical portion so that an inlet of the annular conduit receives the pressurized gas and an outlet of the annular conduit directs the pressurized gas past the opening of the sampling tube;
   wherein the air intake has a longitudinal axis extending therethrough and is circular thereabout; and
   wherein the sampling tube has an inlet opening disposed within the cylindrical portion of the air intake.

2. The apparatus of claim 1, wherein the source of pressurized gas is a manifold which receives the pressurized gas from the exhaust of an air sampling device.

3. The apparatus of claim 1, wherein the sampling tube has a shroud disposed about the inlet opening to direct aerosol-containing air into the sampling tube.

4. The apparatus of claim 1, wherein the sampling tube is concentric with the longitudinal axis extending through the air intake.

5. An apparatus for redirecting a flow of aerosol-containing air, comprising:
   means disposed within the flow of aerosol-containing air,
   means for directing a portion of the aerosol-containing air into the means disposed within the flow of aerosol-containing air; and
   means located within the means disposed within the flow of aerosol-containing air for receiving aerosol-containing air;
   wherein the means for directing a portion of the flow of aerosol-containing air comprises: an air intake comprising a converging inlet portion, an intermediate cylindrical portion and a diverging portion; a source of pressurized gas; an annular conduit within the air intake for directing the pressurized gas past the opening of a sampling tube; and means for injecting the pressurized gas into the air intake so as to cause the flow of the portion of aerosol-containing air in the air intake;
   wherein the annular conduit is disposed outside the intermediate cylindrical portion so that an inlet of the annular conduit receives the pressurized and an outlet of the annular conduit directs the pressurized gas vast the opening of the sampling tube; and
   wherein the sampling tube has an inlet opening disposed within the cylindrical portion of the air intake.

6. A method for redirecting a flow of aerosol-containing air, said method comprising:
   placing an apparatus in the flow of aerosol-containing air; wherein said apparatus comprises:
   an air intake disposed within the flow of aerosol-containing air;
   means for redirecting a portion of the flow of aerosol-containing air into the air intake; and
   a sampling tube having an opening for receiving aerosol-containing air disposed within the air intake;
   wherein the means for redirecting a portion of the flow of aerosol-containing air into the air intake comprises: a source of pressurized gas; and means for injecting the pressurized gas into the air intake so as to cause a flow of the portion of aerosol-containing air in the air intake;
   wherein the means for injecting the pressurized gas into the air intake comprises: an annular conduit within the air intake for directing the pressurized gas downstream of the opening of the sampling tube;
   wherein the air intake comprises: a converging inlet portion, an intermediate cylindrical portion and a diverging portion; and the annular conduit is disposed outside the intermediate cylindrical portion so that an inlet of the annular conduit receives the pressurized gas and an outlet of the annular conduit directs the pressurized gas past the opening of the sampling tube;
   wherein the air intake has a longitudinal axis extending therethrough and is circular thereabout and
   wherein the sampling tube has an inlet opening disposed within the cylindrical portion of the air intake.

* * * * *